United States Patent
O'Mahony et al.

(10) Patent No.: US 10,144,978 B2
(45) Date of Patent: Dec. 4, 2018

(54) PROBIOTIC BIFIDOBACTERIUM STRAIN

(75) Inventors: Liam O'Mahony, Cork (IE); Barry Kiely, Cork (IE); John Francis Cryan, Cork (IE); Timothy Dinan, Cork (IE); Eileen Frances Murphy, Cork (IE)

(73) Assignee: Alimentary Health Ltd., Cork (IE)

( * ) Notice: Subject to any disclaimer, the term of this patent is extended or adjusted under 35 U.S.C. 154(b) by 465 days.

(21) Appl. No.: 13/468,374

(22) Filed: May 10, 2012

(65) Prior Publication Data

US 2012/0276143 A1 Nov. 1, 2012
US 2018/0202010 A9 Jul. 19, 2018

Related U.S. Application Data

(63) Continuation of application No. PCT/IE2010/000066, filed on Nov. 11, 2010, which is a continuation-in-part of application No. 12/616,752, filed on Nov. 11, 2009, now Pat. No. 9,771,624.

(60) Provisional application No. 61/344,030, filed on May 11, 2010.

(51) Int. Cl.
*A61K 39/02* (2006.01)
*A61P 1/00* (2006.01)
*A61P 1/04* (2006.01)
*C12R 1/01* (2006.01)
*A23C 9/123* (2006.01)
*A23G 9/36* (2006.01)
*A61K 35/745* (2015.01)
*C12N 1/20* (2006.01)
*A23L 33/135* (2016.01)

(52) U.S. Cl.
CPC .............. *C12R 1/01* (2013.01); *A23C 9/1234* (2013.01); *A23G 9/363* (2013.01); *A23L 33/135* (2016.08); *A61K 35/745* (2013.01); *C12N 1/20* (2013.01); *A23V 2002/00* (2013.01); *A23Y 2300/55* (2013.01); *Y02A 50/473* (2018.01)

(58) Field of Classification Search
None
See application file for complete search history.

(56) References Cited

U.S. PATENT DOCUMENTS

| 8,343,482 | B2 | 1/2013 | Bergonzelli et al. |
| 2003/0092163 | A1* | 5/2003 | Collins ............... A61K 35/745 435/252.1 |
| 2004/0265279 | A1 | 12/2004 | Dinan et al. |
| 2006/0204485 | A1 | 9/2006 | Dinan et al. |
| 2008/0267933 | A1 | 10/2008 | Ohlson et al. |
| 2010/0183559 | A1* | 7/2010 | Van Sinderen et al. ..... 424/93.2 |

OTHER PUBLICATIONS

Ting Wa, Experimental research on Bifidobacterium-cultivated supernatant fluid regulating blood fat index of aging rats underlined by D-gal., Chinese Journal of Microecology, 2008; 3:016.
Imaoka A., et al., Anti-inflammatory activity of probiotic Bifidobacterium: enhancement of IL-10 production in peripheral blood mononuclear cells from ulcerative colitis patients and inhibition of IL-8 secretion in HT-29 cells, World journal of gastroenterology, Apr. 28, 2008; 14(16):2511.
Chin J Biologicals, Jun. 2009, vol. 22, No. 6, pp. 628-632, Hu Min, etc.
PCT International Search Report and Written Opinion for PCT/IE2010/000066 dated Mar. 23, 2011.
Desbonnet, L. et al., "Effects of the Probiotic *Bifidobacterium infantis* in the Maternal Separation Model of Depression," *Neuroscience*, vol. 170, pp. 1179-1188 (2010).
McKernan, D.P. et al., "The Probiotic *Bifidobacerium infantis* 35624 Display Visceral Antinociceptive Effects in the Rat," *Neurogastroenterol. Motil*, vol. 22, pp. 1029-1035 (2010).
Medina, M. et al., "Differential Immunomodulatory Properties of Bifidobacterium Logum Strains: Relevance to Probiotic Selection and Clinical Applications," *Clinical and Experimental Immunology*, vol. 150, pp. 531-538 (2007).
O'Mahony, L. et al., "Lactobacillus and Bifidobacterium in Irritable Bowel Syndrome: Symptom Responses and Relationship to Cytokine Profiles," *Gastroenterology*, vol. 128, pp. 541-551 (2005).
Whorwell, P.J. et al., "Efficacy of an Encapsulated Probiotic Bifidobacterium Infantis 35624 in Women with Irritable Bowel Syndrome," *Am J Gastroenterol*, vol. 101, pp. 1581-1590 (2006).

* cited by examiner

*Primary Examiner* — Robert A Zeman
(74) *Attorney, Agent, or Firm* — Bookoff McAndrews, PLLC

(57) ABSTRACT

Probiotic *Bifidobacterium* strain AH1714 is significantly immunomodulatory following oral consumption. The strain is useful as an immunomodulatory biotherapeutic agent.

14 Claims, 9 Drawing Sheets

Specification includes a Sequence Listing.

```
                            SEQUENCE LISTING

<160> NUMBER OF SEQ ID NOS: 6

<210> SEQ ID NO 1
<211> LENGTH: 450
<212> TYPE: DNA
<213> ORGANISM: Bifidobacterium longum
<220> FEATURE:
<221> NAME/KEY: misc_feature
<222> LOCATION: (48)..(48)
<223> OTHER INFORMATION: n is a, c, g, or t

<400> SEQUENCE: 1
ttctccgagg tgtgcgcccc gcgcgtcgca tggtgcgatg gcggcggngt tgctggtgtg      60
gaagacgtcg ttggctttgc cctgccggtc gtgcggtggg tgcggggtgg tatggatgcg    120
cttttgggct cccggatcgc cacccaggc tttttgcctg gcgcgattcg atgcccgtcg     180
tgcctggggg ccggccgtgt gccggcgcga tggcgtggcg gtgcgtggtg gcttgagaac    240
tggatagtgg acgcgagcaa aacaagagtt tttgaatctt tgttttgctg ttgatttcga    300
atcgaactct attgttcgtt tcgatcgttt tgtgatcatt tttagtgtga tgatttgtcg    360
tctgggaatt tgctagagga atcttgcggc catgcacttt cgtggtgtgt gttgcttgca    420
agggcgtatg gtggatgcct tgacaccaga                                     450

<210> SEQ ID NO 2
<211> LENGTH: 462
<212> TYPE: DNA
<213> ORGANISM: Bifidobacterium longum
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (454)..(454)
<223> OTHER INFORMATION: n is a, c, g, or t

<400> SEQUENCE: 2
cacacacacc cacgnaagtg tcatggcccg caagtatttc ctctagcaaa ttcccagnac      60
gacaaatcat cacactaaaa atgatcacaa aacgatcgaa acgaacaata gagttcgatt    120
```

```
cgaaatcaac agcaaaacaa agattcaaaa actcttgttt tgctcgcgtc cactatccag      180
ttctcaagcc accacgcacc gccacgccat cgcgccggca cacggccggc ccccaggcac      240
gacgggcatc gaatcgcgcc aggcaaaaag cctggggtgg cgatccggga gcccaaaagc      300
gcatccatac caccccgcac ccaccgcacg accggcaggg caaagccaac gacgtcttcc      360
acaccagcaa ccccgccgcc atcgcaccat gcgacgcgcg gggcgcacac cgtcggacga      420
acatccgact gaattctccg tagaaaggag gtgntcccag ca                         462

<210> SEQ ID NO 3
<211> LENGTH: 19
<212> TYPE: DNA
<213> ORGANISM: Unknown
<220> FEATURE:
<223> OTHER INFORMATION: synthesised sequence

<400> SEQUENCE: 3
gctggatcac ctcctttct                                                   19

<210> SEQ ID NO 4
<211> LENGTH: 18
<212> TYPE: DNA
<213> ORGANISM: Unknown
<220> FEATURE:
<223> OTHER INFORMATION: synthesised sequence

<400> SEQUENCE: 4
ctggtgccaa ggcatcca                                                    18

<210> SEQ ID NO 5
<211> LENGTH: 22
<212> TYPE: DNA
<213> ORGANISM: Unknown
<220> FEATURE:
<223> OTHER INFORMATION: synthesised sequence

<400> SEQUENCE: 5
ctacggcaag gcgacgctga cg                                               22

<210> SEQ ID NO 6
<211> LENGTH: 493
<212> TYPE: DNA
<213> ORGANISM: Bifidobacterium longum

<400> SEQUENCE: 6
tgctgggatc acctcctttc tacggagaat tcagtcggat gttcgtccga cggtgtgcgc      60
cccgcgcgtc gcatggtgcg atggcggcgg ggttgctggt gtggaagacg tcgttggctt      120
tgccctgccg gtcgtgcggt gggtgcgggg tggtatggat gcgcttttgg gctcccggat      180 cgccaccccca ggcttttgc ctggcgcgat tcgatgcccg tcgtgcctgg gggcggccg      240 tgtgccggcg cgatggcgtg gcggtgcgtg gtggcttgag aactggatag tggacgcgag      300
caaaacaaga gtttttgaat ctttgttttg ctgttgattt cgaatcgaac tctattgttc      360
gtttcgatcg ttttgtgatc atttttagtg tgatgatttg tcgtctggga atttgctaga      420
ggaatcttgc ggccatgcac tttcgtggtg tgtgttgctt gcaagggcgt atggtggatg      480
ccttgacacc aga                                                         493
```

PROBIOTIC BIFIDOBACTERIUM STRAIN

CROSS REFERENCE TO RELATED APPLICATIONS

This application is a continuation application of prior International Application No. PCT/IE2010/000066 filed on Nov. 11, 2010 which is a continuation-in-part of U.S. application Ser. No. 12/616,752 filed Nov. 11, 2009, now U.S. Pat. No. 9,771,624, and claims the benefit of U.S. Provisional Application No. 61/344,030 filed May 11, 2010.

INTRODUCTION

The invention relates to a *Bifidobacterium* strain and its use as a probiotic bacteria in particular as an immunomodulatory biotherapeutic agent.

The defense mechanisms to protect the human gastrointestinal tract from colonization by intestinal bacteria are highly complex and involve both immunological and non-immunological aspects (1). Innate defense mechanisms include the low pH of the stomach, bile salts, peristalsis, mucin layers and anti-microbial compounds such as lysozyme (2). Immunological mechanisms include specialized lymphoid aggregates, underlying M cells, called peyers patches which are distributed throughout the small intestine and colon (3). Luminal antigens presented at these sites result in stimulation of appropriate T and B cell subsets with establishment of cytokine networks and secretion of antibodies into the gastrointestinal tract (4). In addition, antigen presentation may occur via epithelial cells to intraepithelial lymphocytes and to the underlying lamina propria immune cells (5). Therefore, the host invests substantially in immunological defense of the gastrointestinal tract. However, as the gastrointestinal mucosa is the largest surface at which the host interacts with the external environment, specific control mechanisms must be in place to regulate immune responsiveness to the 100 tons of food which is handled by the gastrointestinal tract over an average lifetime. Furthermore, the gut is colonized by over 500 species of bacteria numbering $10^{11}$-$10^{12}$/g in the colon. Thus, these control mechanisms must be capable of distinguishing non-pathogenic adherent bacteria from invasive pathogens, which would cause significant damage to the host. In fact, the intestinal flora contributes to defense of the host by competing with newly ingested potentially pathogenic micro-organisms.

Bacteria present in the human gastrointestinal tract can promote inflammation. Aberrant immune responses to the indigenous microflora have been implicated in certain disease states, such as inflammatory bowel disease. Antigens associated with the normal flora usually lead to immunological tolerance and failure to achieve this tolerance is a major mechanism of mucosal inflammation (6). Evidence for this breakdown in tolerance includes an increase in antibody levels directed against the gut flora in patients with inflammatory bowel disease (IBD).

The present invention is directed towards a *Bifidobacterium* strain which has been shown to have immunomodulatory effects, by modulating cytokine levels or by antagonizing and excluding pro-inflammatory micro-organisms from the gastrointestinal tract.

STATEMENTS OF INVENTION

The invention provides an isolated strain of *Bifidobacterium* NCIMB 41676.

The *Bifidobacterium* strain may be in the form of viable cells. The *Bifidobacterium* strain may be in the form of non-viable cells. The *Bifidobacterium* may be isolated from colonic biopsy tissue from a healthy human subject. The *Bifidobacterium* strain may be significantly immunomodulatory following oral consumption in humans.

The invention also provides a formulation which comprises a *Bifidobacterium* strain as described herein. The formulation may further comprise a probiotic material. The formulation may further comprise a prebiotic material. The formulation may further comprise an ingestable carrier. The ingestable carrier may a pharmaceutically acceptable carrier such as a capsule, tablet or powder. The ingestable carrier may be a food product such as acidified milk, yoghurt, frozen yoghurt, milk powder, milk concentrate, cheese spreads, dressings or beverages. The formulation may further comprise a protein and/or peptide, in particular proteins and/or peptides that are rich in glutamine/glutamate, a lipid, a carbohydrate, a vitamin, mineral and/or trace element. The *Bifidobacterium* strain may be present in an amount of more than $10^6$ cfu per gram of the formulation. The formulation may further comprise an adjuvant. The formulation may further comprise a bacterial component. The formulation may further comprise a drug entity. The formulation may further comprise a biological compound. The formulation may be used for immunisation and vaccination protocols.

The invention also provides a *Bifidobacterium* strain or a formulation as described herein for use in foodstuffs.

The invention also provides a *Bifidobacterium* strain or a formulation as described herein for use as a medicament.

The invention also provides a *Bifidobacterium* strain or a formulation as described herein for use in the prophylaxis and/or treatment of undesirable inflammatory activity.

The invention also provides a *Bifidobacterium* strain or a formulation as described herein for use in the prophylaxis and/or treatment of undesirable gastrointestinal inflammatory activity such as inflammatory bowel disease eg. Crohns disease or ulcerative colitis, irritable bowel syndrome; pouchitis; or post infection colitis.

The invention also provides a *Bifidobacterium* strain or a formulation as described herein for use in the prophylaxis and/or treatment of gastrointestinal cancer(s).

The invention also provides a *Bifidobacterium* strain or a formulation as described herein for use in the prophylaxis and/or treatment of systemic disease such as rheumatoid arthritis.

The invention also provides a *Bifidobacterium* strain or a formulation as described herein for use in the prophylaxis and/or treatment of autoimmune disorders due to undesirable inflammatory activity.

The invention also provides a *Bifidobacterium* strain or a formulation as described herein for use in the prophylaxis and/or treatment of cancer due to undesirable inflammatory activity.

The invention also provides a *Bifidobacterium* strain or a formulation as described herein for use in the prophylaxis of cancer.

The invention also provides a *Bifidobacterium* strain or a formulation as described herein for use in the prophylaxis and/or treatment of diarrhoeal disease due to undesirable inflammatory activity, such as *Clostridium difficile* associated diarrhoea, Rotavirus associated diarrhoea or post infective diarrhoea or diarrhoeal disease due to an infectious agent, such as *E. coli*.

The invention also provides a *Bifidobacterium* strain or a formulation as described herein for use in the preparation of anti-inflammatory biotherapeutic agents for the prophylaxis and/or treatment of undesirable inflammatory activity.

*Bifidobacterium* strains as described herein may be used in the preparation of a panel of biotherapeutic agents for modifying the levels of IL-10.

The invention also provides a *Bifidobacterium* strain or a formulation as described herein for use in the prevention and/or treatment of inflammatory disorders, immunodeficiency, inflammatory bowel disease, irritable bowel syndrome, cancer (particularly of the gastrointestinal and immune systems), diarrhoeal disease, antibiotic associated diarrhoea, paediatric diarrhoea, appendicitis, autoimmune disorders, multiple sclerosis, Alzheimer's disease, rheumatoid arthritis, coeliac disease, diabetes mellitus, organ transplantation, bacterial infections, viral infections, fungal infections, periodontal disease, urogenital disease, sexually transmitted disease, HIV infection, HIV replication, HIV associated diarrhoea, surgical associated trauma, surgical-induced metastatic disease, sepsis, weight loss, anorexia, fever control, cachexia, wound healing, ulcers, gut barrier function, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, epidermal disorders, psoriasis, acne vulgaris, panic disorder, behavioral disorder and/or post traumatic stress disorders.

The *Bifidobacterium* strain as described herein may act by antagonising and excluding proinflammatory micro-organisms from the gastrointestinal tract.

The invention also provides a *Bifidobacterium* strain or a formulation as described herein for use in the preparation of anti-inflammatory biotherapeutic agents for reducing the levels of pro inflammatory cytokines.

The *Bifidobacterium* strain as described herein may be used as an anti-infective probiotic strain.

The invention also provides a *Bifidobacterium* strain or a formulation as described herein for use in the prophylaxis and/or treatment of bipolar illness, depression, mood disorders, and/or anxiety disorders.

The invention also provides a *Bifidobacterium* strain or a formulation as described herein may be used as a cognative enhancer for the prophylaxis and/or treatment of disorders of the central nervous system such as Alzheimer's disease, schizophrenia and/or mild cognative disorder.

The invention also provides a *Bifidobacterium* strain or a formulation as described herein for use in the prophylaxis and/or treatment of obesity related inflammation.

The invention also provides a *Bifidobacterium* strain or a formulation as described herein for use in the prophylaxis and/or treatment of obesity related metabolic dysregulation.

We describe *Bifidobacterium* strain AH1714 (NCIMB 41676) or mutants or variants thereof. The mutant may be a genetically modified mutant. The variant may be a naturally occurring variant of *Bifidobacterium*. Also described is a rifampicin resistant variant of strain AH1714. The strain may be a probiotic. It may be in the form of a biologically pure culture.

We also describe an isolated strain of *Bifidobacterium* NCIMB 41676. The *Bifidobacterium* strains may be in the form of viable cells. Alternatively *Bifidobacterium* strains are in the form of non-viable cells. The general use of probiotic bacteria is in the form of viable cells. However, it can also be extended to non-viable cells such as killed cultures or compositions containing beneficial factors expressed by the probiotic bacteria. This could include thermally killed micro-organisms or micro-organisms killed by exposure to altered pH or subjection to pressure or gamma irradiation. With non-viable cells product preparation is simpler, cells may be incorporated easily into pharmaceuticals and storage requirements are much less limited than viable cells. *Lactobacillus casei* YIT 9018 offers an example of the effective use of heat killed cells as a method for the treatment and/or prevention of tumour growth as described in U.S. Pat. No. 4,347,240.

The *Bifidobacterium* strains may be isolated from colonic biopsy tissue from healthy human subjects, the *Bifidobacterium* strains being significantly immunomodulatory following oral consumption in humans.

We also describe a formulation which comprises the *Bifidobacterium* strain as described herein. The formulation may include another probiotic material. The formulation may include a prebiotic material. Preferably the formulation includes an ingestable carrier. The ingestable carrier may be a pharmaceutically acceptable carrier such as a capsule, tablet or powder. Preferably the ingestable carrier is a food product such as acidified milk, yoghurt, frozen yoghurt, milk powder, milk concentrate, cheese spreads, dressings or beverages. The formulation may further comprise a protein and/or peptide, in particular proteins and/or peptides that are rich in glutamine/glutamate, a lipid, a carbohydrate, a vitamin, mineral and/or trace element. The *Bifidobacterium* strain may be present in the formulation at more than $10^6$ cfu per gram of delivery system. Preferably the formulation includes any one or more of an adjuvant, a bacterial component, a drug entity or a biological compound.

We also describe a *Bifidobacterium* strain or a formulation for use as foodstuffs, as a medicament, for use in the prophylaxis and/or treatment of undesirable inflammatory activity, for use in the prophylaxis and/or treatment of undesirable respiratory inflammatory activity such as asthma, for use in the prophylaxis and/or treatment of undesirable gastrointestinal inflammatory activity such as inflammatory bowel disease eg. Crohns disease or ulcerative colitis, irritable bowel syndrome, pouchitis, or post infection colitis, for use in the prophylaxis and/or treatment of gastrointestinal cancer(s), for use in the prophylaxis and/or treatment of systemic disease such as rheumatoid arthritis, for use in the prophylaxis and/or treatment of autoimmune disorders due to undesirable inflammatory activity, for use in the prophylaxis and/or treatment of cancer due to undesirable inflammatory activity, for use in the prophylaxis of cancer, for use in the prophylaxis and/or treatment of diarrhoeal disease due to undesirable inflammatory activity, such as *Clostridium difficile* associated diarrhoea, Rotavirus associated diarrhoea or post infective diarrhoea, for use in the prophylaxis and/or treatment of diarrhoeal disease due to an infectious agent, such as *E. coli*.

We also describe a *Bifidobacterium* strain or a formulation of the invention for use in the preparation of an anti-inflammatory biotherapeutic agent for the prophylaxis and/or treatment of undesirable inflammatory activity or for use in the preparation of anti-inflammatory biotherapeutic agents for the prophylaxis and/or treatment of undesirable inflammatory activity. The strain may act by antagonising and excluding proinflammatory micro-organisms from the gastrointestinal tract.

We also describe a *Bifidobacterium* strain or a formulation for use in the preparation of anti-inflammatory biotherapeutic agents for reducing the levels of pro-inflammatory cytokines.

The *Bifidobacterium* strain may be used in the preparation of anti-inflammatory biotherapeutic agents for modifying the levels of IL-10.

The *Bifidobacterium* strain may be used as a anti-infective probiotic due to their ability to antagonise the growth of pathogenic species.

We have found that particular strains of *Bifidobacterium* elicit immunomodulatory effects in vitro.

The invention is therefore of major potential therapeutic value in the prophylaxis or treatment of dysregulated immune responses, such as undesirable inflammatory reactions for example asthma.

*Bifidobacterium* are commensal microorganisms. They have been isolated from the microbial flora within the human gastrointestinal tract. The immune system within the gastrointestinal tract cannot have a pronounced reaction to members of this flora, as the resulting inflammatory activity would also destroy host cells and tissue function. Therefore, some mechanism(s) exist whereby the immune system can recognize commensal non-pathogenic members of the gastrointestinal flora as being different to pathogenic organisms. This ensures that damage to host tissues is restricted and a defensive barrier is still maintained.

A deposit of *Bifidobacterium longum* strain AH1714 was made under the terms of the Budapest Treaty at the National Collections of Industrial and Marine Bacteria Limited (NCIMB) Ferguson Building, Craibstone Estate, Bucksburn, Aberdeen, AB21 9YA, Scotland, UK on Nov. 5, 2009 and accorded the accession number NCIMB 41676.

The *Bifidobacterium longum* may be a genetically modified mutant or it may be a naturally occurring variant thereof.

Preferably the *Bifidobacterium longum* may be in the form of viable cells.

Alternatively the *Bifidobacterium longum* may be in the form of non-viable cells.

It will be appreciated that the specific *Bifidobacterium* strain of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound.

In addition a vaccine comprising the strains of the invention may be prepared using any suitable known method and may include a pharmaceutically acceptable carrier or adjuvant.

Throughout the specification the terms mutant, variant and genetically modified mutant include a strain of Bifidobacteria whose genetic and/or phenotypic properties are altered compared to the parent strain. Naturally occurring variant of *Bifidobacterium longum* includes the spontaneous alterations of targeted properties selectively isolated. Deliberate alteration of parent strain properties is accomplished by conventional (in vitro) genetic manipulation technologies, such as gene disruption, conjugative transfer, etc. Genetic modification includes introduction of exogenous and/or endogenous DNA sequences into the genome of a Bifidobacteria strain, for example by insertion into the genome of the bacterial strain by vectors, including plasmid DNA, or bacteriophages.

Natural or induced mutations include at least single base alterations such as deletion, insertion, transversion or other DNA modifications which may result in alteration of the amino acid sequence encoded by the DNA sequence.

The terms mutant, variant and genetically modified mutant also include a strain of Bifidobacteria that has undergone genetic alterations that accumulate in a genome at a rate which is consistent in nature for all micro-organisms and/or genetic alterations which occur through spontaneous mutation and/or acquisition of genes and/or loss of genes which is not achieved by deliberate (in vitro) manipulation of the genome but is achieved through the natural selection of variants and/or mutants that provide a selective advantage to support the survival of the bacterium when exposed to environmental pressures such as antibiotics. A mutant can be created by the deliberate (in vitro) insertion of specific genes into the genome which do not fundamentally alter the biochemical functionality of the organism but whose products can be used for identification or selection of the bacterium, for example antibiotic resistance.

A person skilled in the art would appreciate that mutant or variant strains of Bifidobacteria can be identified by DNA sequence homology analysis with the parent strain. Strains of Bifidobacteria having a close sequence identity with the parent strain are considered to be mutant or variant strains. A Bifidobacteria strain with a sequence identity (homology) of 96% or more, such as 97% or more, or 98% or more, or 99% or more with the parent DNA sequence may be considered to be a mutant or variant. Sequence homology may be determined using on-line homology algorithm "BLAST" program, publicly available at http://www.ncbi.nlm.nih,gov/BLAST/.

Mutants of the parent strain also include derived Bifidobacteria strains having at least 85% sequence homology, such as at least 90% sequence homology, or at least 95% sequence homology to the 16s-23s intergenic spacer polynucleotide sequence of the parent strain. These mutants may further comprise DNA mutations in other DNA sequences in the bacterial genome.

BRIEF DESCRIPTION OF THE DRAWINGS

The invention will be more clearly understood from the following description thereof given by way of example only with reference to the accompanying drawings in which;—

Figure 8:
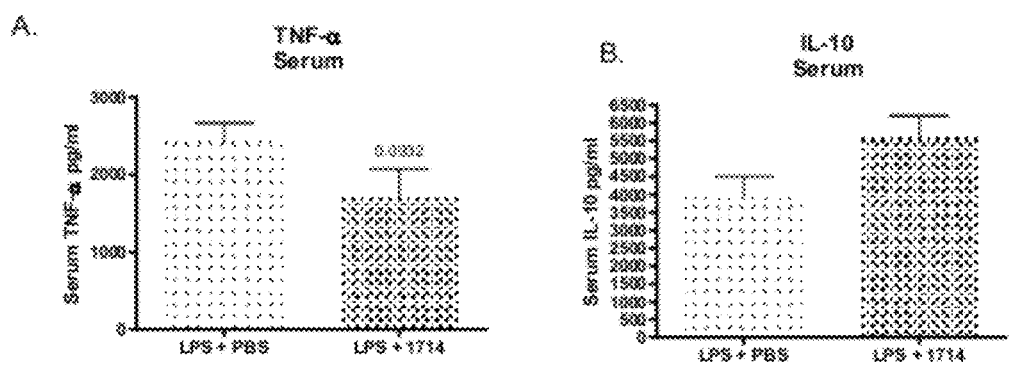
Figure 9:
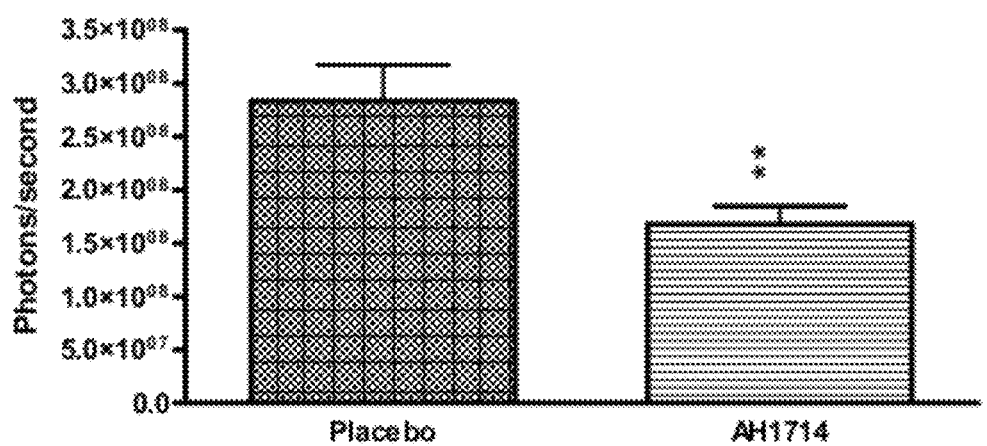
Figure 10:
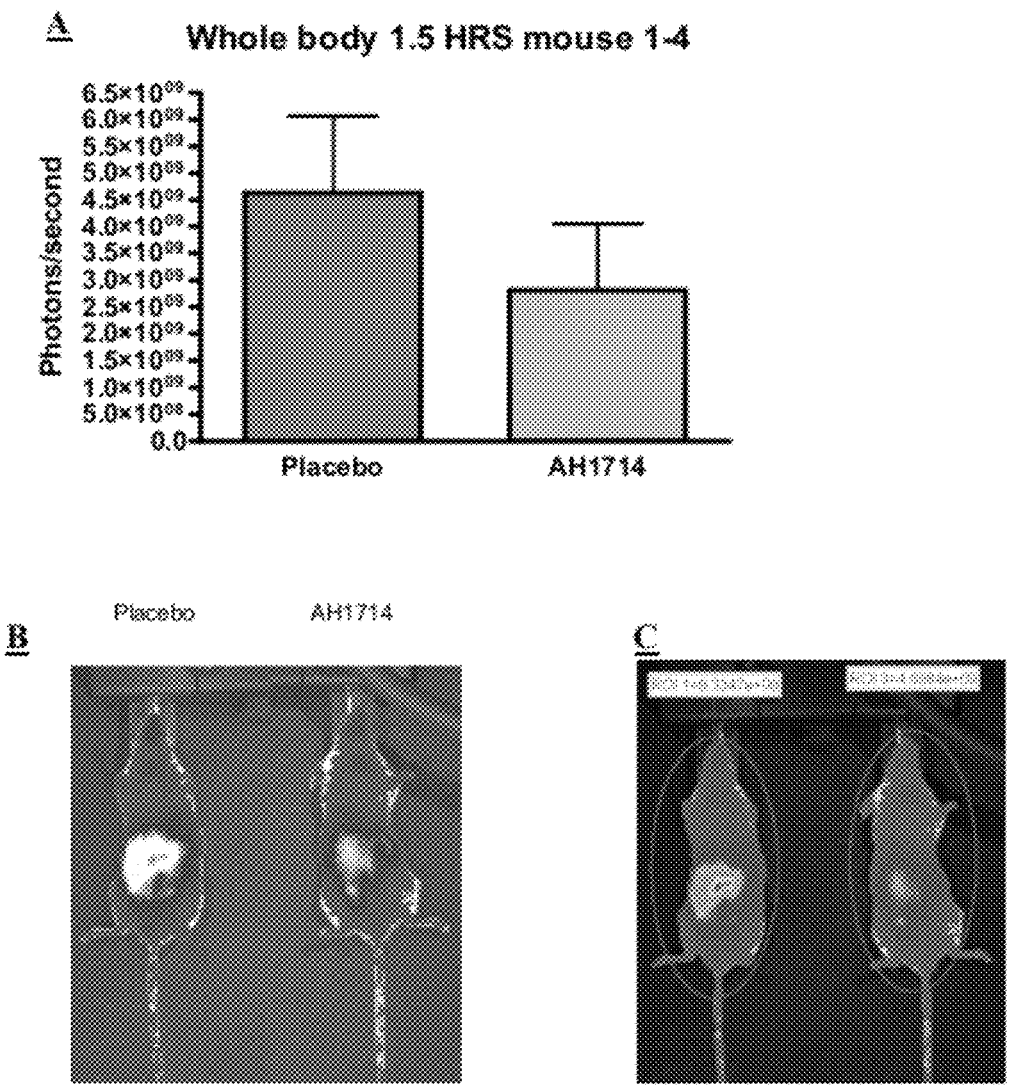
Figure 11:
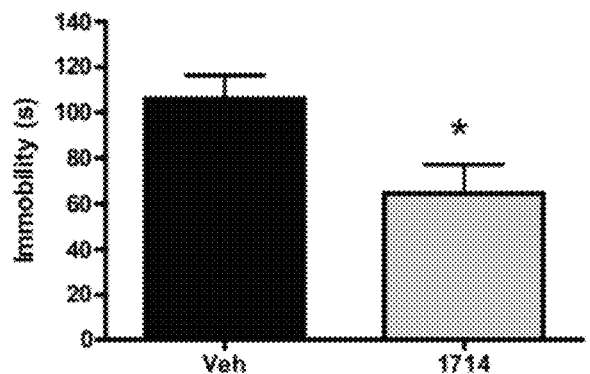
Figure 12:
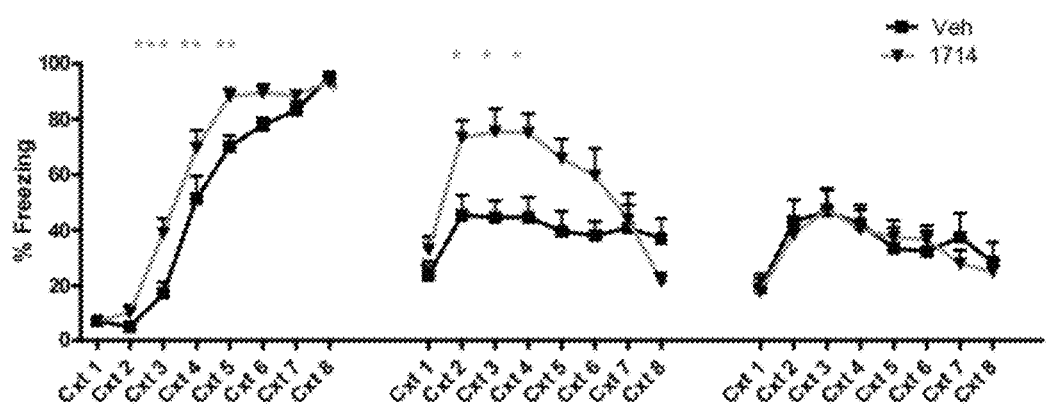
Figure 13:
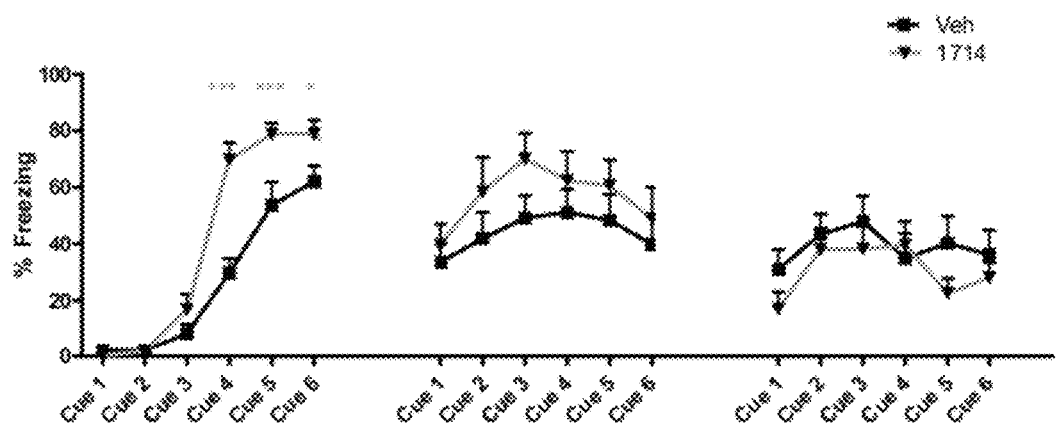
Figure 14:
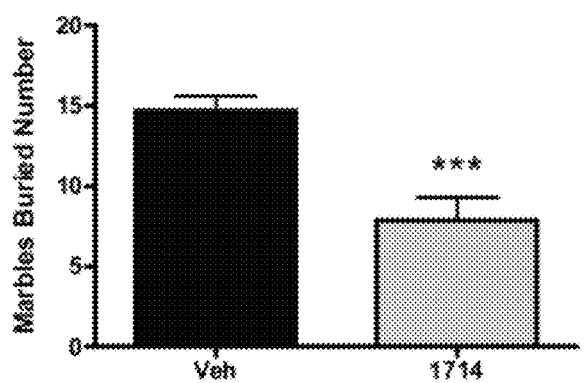
Figure 15:
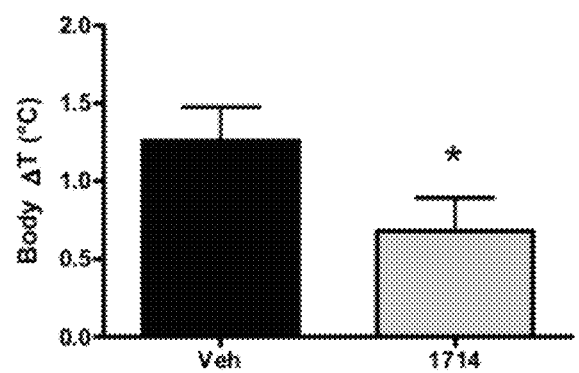
Figure 16:
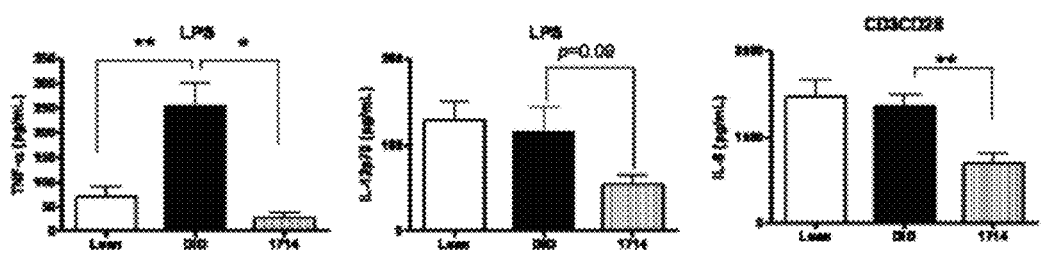

In vitro cells are either unstimulated (A) or stimulated with antiCD3/CD28 (B). Data is shown as Average & SEM;

FIG. 8 is a bar chart showing the induction profile of TNF-α (A) and IL-10 (B) in serum sampled from both 1714 and PBS fed mice post 2H in vivo challenge with LPS 1 mg/kg. Data is shown as Average & SEM;

FIG. 9 is a bar chart showing NFkB activity (Photons/second) from isolated spleen 3 hours post challenge with a single 0.5 mg/kg dose of LPS, from Placebo and 1714-fed animals (** designates $p<0.01$);

FIG. 10 is a bar chart (A) showing NFkB activity (Photons/second) from whole body imaging 1.5 hours post challenge with a single 0.5 mg/kg dose of LPS, from Placebo and 1714-fed animals ((B) and (C) are whole body representative images in black and white and colour;

FIG. 11 is a bar chart representing the time of immobility displayed by the mice over a 6-min test;

FIG. 12 is a line graph representing the freezing percentage in response to the fearful stimulus (context) for day 1 (acquisition), day 2 (memory/extinction) and day 3 (extinction);

FIG. 13 is a line graph representing the freezing percentage in response to the fearful stimulus (cue) for day 1 (acquisition), day 2 (memory/extinction) and day 3 (extinction);

FIG. 14 is a bar chart representing the number of marbles buried by the mice over a 30-min session;

FIG. 15 is a bar chart representing the body temperature variation (ΔT) mice displayed following handling; and FIG. 16 is a bar chart showing the changes in cytokine levels in stimulated splenocytes from the Diet Induced Mouse model.

DETAILED DESCRIPTION OF THE INVENTION

A deposit of *Bifidobacterium longum* strain AH1714 was made at the National Collections of Industrial and Marine Bacteria Limited (NCIMB) Ferguson Building, Craibstone Estate, Bucksburn, Aberdeen, AB21 9YA, Scotland, UK on Nov. 5, 2009 and accorded the accession number NCIMB 41676.

A deposit of *Bifidobacterium longum* strain UCC35624 was made at the National Collections of Industrial and Marine Bacteria Limited (NCIMB) Ferguson Building, Craibstone Estate, Bucksburn, Aberdeen, AB21 9YA, Scotland, UK on Jan. 13, 1999 and accorded the accession number NCIMB 41003.

EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention.

Example 1—Isolation of *Bifidobacterium longum* AH1714

*Bifidobacterium longum* strain AH1714 was isolated from colonic biopsy tissue from healthy human subjects.

Sections of the large of the human G.I.T, obtained during colorectal scoping, were screened for probiotic bacterial strains. Musocal tissue from the human gastrointestinal tract was transferred to a collection tube containing Phosphate Buffered Saline (PBS), supplemented with 0.05% cysteine-HCl). Triton X-100 (0.05%) was added to release the adherent microorganisms from the tissue sample. Tissue samples were then incubated for 10 min. The samples were vortexed vigorously and adherent Lactobacilli and Bifidobacteria isolated from the gastrointestinal tissue by plating on selective agar (De Man, Rogosa and Sharpe (MRS) agar+Vancomycin and Wilkins-Chalgren Agar+Mupirocin, respectively). Isolated colonies were picked from the plates and re-streaked three times to ensure purity. Microscope examination, Gram staining, Catalase testing, Fructose-6-Phosphate Phosphoketolase assessment were used to determine presumptive Bifidobacteria species and isolates were stocked in 40% glycerol and stored at −20° and −80° C. 16S intergenic spacer region sequencing were used to confirm the identity of the newly isolated strains.

Following isolation of a pure bifidobacteria strain, assigned the designation AH1714, microbiological characteristics were assessed and are summarized in Table 1 below. AH1714 is a gram positive, catalase negative pleomorphic shaped bacterium which is Fructose-6-Phoshate Phosphoketolase positive, confirming its identity as a *bifidobacterium*.

TABLE 1

| Physiochemical characteristics of *B. longum* AH1714 | |
|---|---|
| Strain Characteristics | *B. longum* AH1714 |
| Gram Stain | + |
| Catalase | − |
| Motility | − |
| F6PPK* | + |

16s-23s intergenic spacer (IGS) sequencing was performed to identify the species of Bifidobacteria isolated. Briefly, DNA was isolated from AH1714 using 100 μl of Extraction Solution and 25 μl of Tissue Preparation solution (Sigma, XNAT2 Kit). The samples were incubated for 5 minutes at room temperature followed by 2 hrs at 95° C. and then 100 μl of Neutralization Solution (Sigma, XNAT2 kit) was added. Genomic DNA solution was quantified using a Nanodrop spectrophotometer and stored at 4° C. PCR was performed using the IGS primers. The primer pairs used were IGS R 5'-CTGGTGCCAAGGCATCCA-3' (SEQ ID No. 4) and IGS L 5'-GCTGGATCACCTCCTTTCT-3' (SEQ ID No. 3). The cycling conditions were 94° C. for 4 min (1 cycle), 94° C. for 45 sec, 53° C. for 45 sec, 72° C. for 45 sec (28 cycles). The PCR reaction contained 2 μl (100 ng) of DNA, PCR mix (Sigma, Red Taq), 0.025 nM IGS L and R primer (MWG Biotech, Germany). The PCR reactions were performed on a Biotherma thermocycler. The PCR products (10 μl) were ran alongside a molecular weight marker (100 bp Ladder, Roche) on a 2% agarose EtBr stained gel in TAE, to determine the IGS profile. PCR products of *Bifidobacterium* (single band) were purified using the Promega Wizard PCR purification kit. The purified PCR products were sequenced using the primer sequences (above) for the intergenic spacer region. Sequence data was then searched against the NCBI nucleotide database to determine the identity of the strain by nucleotide homology. The resultant DNA sequence data was subjected to the NCBI standard nucleotide-to-nucleotide homology BLAST search engine (http://www.ncbi.nlm.nih.gov/BLAST/). The nearest match to the sequence was identified and then the sequences were aligned for comparison using DNASTAR MegAlign software. The sequences (SEQ ID NO. 1 [IGS forward sequence] and SEQ ID NO. 2

[IGS reverse sequence]) obtained can be viewed in the sequence listing. Searching the NCIMB database revealed that AH1714 has a unique IGS (SEQ ID NO. 1 [forward sequence] and SEQ ID NO. 2 [reverse sequence]) sequence with its closest sequence homology to a *Bifidobacterium longum*.

In order to develop a barcode PCR profile for AH1714, PCR was performed using BOX primers (8). The cycling conditions were 94° C. for 7 min (1 cycle); 94° C. for 1 minute, 53° C. for 45 secs, 65° C. for 8 minutes, (30 cycles) and 65° C. for 16 minutes. The PCR reaction contained 50 ng of DNA, PCR mix (Sigma, Red Taq) and 0.03 nM BOXA1R primer (5'-CTACGGCAAGGCGACGCTGACG-3') (SEQ ID NO. 5) (MWG Biotech, Germany). The PCR reactions were performed on a Biotherma thermocycler. The PCR products were run on a 3% agarose gel alongside a molecular weight marker (Roche, 100 bp ladder) and imaged.

Antibiotic Sensitivity Profiles

The antibiotic sensitivity profiles for *B. longum* AH1714 was determined using the 'disc susceptibility' assay. The cultures were grown up in the appropriate broth medium for 48 h and spread-plated (100 µl) onto agar media. Discs containing known concentrations of the antibiotics were placed onto the agar. Strains were examined for antibiotic sensitivity after 1-2 days incubation at 37° C. under anaerobic conditions.

TABLE 2 antibiotic resistance

| Antibiotic | Group | AH1714 |
|---|---|---|
| Penicillin G | β-lactam antibiotic | S |
| Ampicillin | β-lactam antibiotic | S |
| Methicillin | β-lactam antibiotic | M |
| Streptomycin | Aminoglycoside antibiotic | R |
| Gentamicin | Aminoglycoside antibiotic | M |
| Vancomycin | Glycopeptide antibiotic | S |
| Nalidixic Acid | Synthetic quinolone antibiotic | R |
| Novobiocin | Aminocoumarin antibiotic | S |
| Tetracycline | Polyketide antibiotic | S |
| Sulphamethoxazole | Sulfonamide antibiotic | R |
| Trimethoprim\Sulphamethoxazole | Sulfonamide antibiotic | R |
| Trimethoprim | | R |
| Rifampicin | Rifamycin antibiotic | S |
| Chloramphenicol | | S |
| Metronidazole | Nitroimidazole antibiotics | M |
| Mupirocin | | R |

R = Resistant (Zones size ≤14 mm)
M = Moderately sensitive (Zone size 15-19 mm)
S = Sensitive (Zone size ≥20 mm)

Intestinal Transit

To determine whether *Bifidobacterium longum* AH1714 could survive at low pH values equivalent to those found in the stomach, bacterial cells were harvested from fresh overnight cultures, washed twice in phosphate buffer (pH 6.5) and resuspended in TPY broth adjusted to pH 2.5 (with 1M HCl). Cells were incubated at 37° C. and survival measured at intervals of 5, 30, 60 and 120 minutes using the plate count method. AH1714 survived well for 5 minutes at pH 2.5 while no viable cells were recovered after 30 minutes.

Upon exiting the stomach, putative probiotics are exposed to bile salts in the small intestine. In order to determine the ability of *B. longum* AH1714 to survive exposure to bile, cultures were streaked on TPY agar plates supplemented with 0.3% (w/v), 0.5%, 1%, 2%, 5%, 7.5% or 10% porcine bile. *B. longum* AH1714 growth was observed on plates containing up to 0.5% bile.

TABLE 3

Growth of AH1714 in the presence of porcine bile (duplicate results)

| | % (w/v) Porcine bile | | | | | | | |
|---|---|---|---|---|---|---|---|---|
| Strain | 0.0 | 0.3 | 0.5 | 1.0 | 2.0 | 5.0 | 7.5 | 10.0 |
| AH 1714 | +++ | ++ | + | − | − | − | − | − |

+++ = very good growth ~100%
++ = good growth ~66%
+ = poor growth ~33%
− = no growth ~0%

Figure 1:
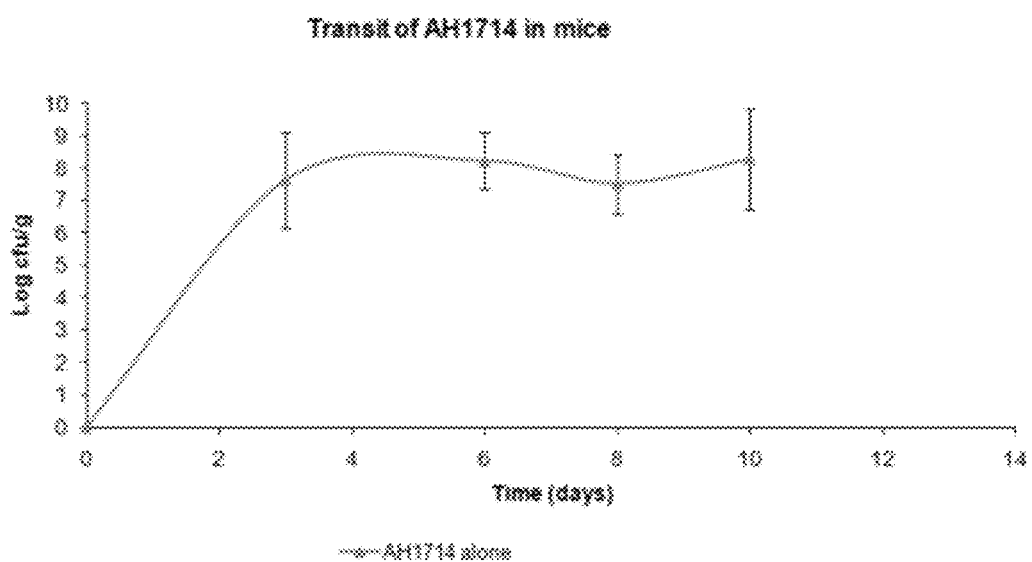
FIG. 1 is a graph illustrating transit of *B. longum* AH1714 through the gastrointestinal tract.

In a germ-free murine model, the ability of *B. longum* AH1714 to transit the gastrointestinal tract was assessed. Mice consumed $1 \times 10^9$ AH1714 daily and faecal pellets were examined for the presence of the fed micro-organism. Detection of AH1714 was facilitated by isolating a spontaneous rifampicin resistant variant of the bifidobacteria—incorporation of rifampicin in the RCA+cysteine plates used to assess transit ensured that only the fed rifampicin resistant bifiobacteria was cultured. Faecal samples were collected daily and *B. longum* AH1714 transit through the gastrointestinal tract was confirmed (See FIG. 1)

Anti-Microbial Activity

To assess the antimicrobial activities of *B. longum* AH1714 against indicator cultures and to determine if the antimicrobial activity was due to acid production, AH1714 was grown overnight in MRS (supplemented with 0.05% cysteine-HCl). 2 µl of AH1714 culture was spotted onto the agar and incubated for 24 h. The indicator organisms were grown in TSB (*E. coli* and *Salmonella typhimurium*), Brucella broth (*Campylobacter jejuni*) and Reinforced Clostridia Media (RCM, *Clostridium difficile*). The indicator lawn was prepared by inoculating a molten overlay with 2% (v/v) of the overnight indicator culture, which was poured onto the surface of the spotted probiotic cultures following overnight growth on the agar plates. Plates were incubated at 37° C. under suitable conditions for the indicator strain and the growth recorded after 24-48 hr. Zones of clearing greater than 1 mm diameter were considered sensitive to the probiotic strain. This assay was also performed on media supplemented with 2% β-glycerophosphate as a buffering agent to limit antagonistic activity due to acid production.

TABLE 4 antimicrobial activity of AH1714

| | Zone of inhibition (mm) | |
|---|---|---|
| Indicator strain | Non-Buffered | Buffered |
| *Campylobacter jejuni* | 9 | 9 |
| *Clostridium perfringens* | 20 | 10 |
| *Salmonella typhimurium* | 19 | 11 |
| *E. coli* O157:H7 | 16 | 11 |

Generation of Rifampicin ($Rif^R$) Resistant Strains of 1714

In order to track transit of AH1714 in faecal samples, a spontaneous rifampicin-resistant variant (rif+) was isolated as follows: a fresh broth culture of AH1714 was spread-plated (100 µL) onto MRS+rifampicin+cysteine with the lowest concentration of rifampicin (range was 0.1%, 0.08%, 0.06%, 0.04%, 0.02% and 0.002%). Plate media without rifampicin was included as a positive control. Both sets of plates were incubated anaerobically at 37° C. (48 hours). The removed plates were assessed for purity before picking one colony from the rifampicin supplemented agar plate and streaking onto the rifampicin supplemented plate of next highest concentration. In addition, a colony was streaked from the MRS agar plate onto a fresh MRS agar plate and both sets of plates incubated anaerobically at 37° C. (48 hours). This process was repeated for the full range of rifampicin supplemented plates. A single colony from a fully grown culture on a 50 μg/mL rifampicin supplemented MRS agar plate was used to inoculate into 20 ml MRS broth and the resultant culture used for subsequent stocking. The identity of the variant was confirmed by microscopic assessment, IGS sequence analysis and by specific PCR analysis.

Example 2—Congo Red Agar Screen

A Congo red agar screen was used to phenotypically screen for EPS expressing bacterial strains. Briefly, 10 ml Modified Rogosa broth media (+0.05% cysteine) was inoculated aseptically with a freshly grown colony of the bacterial strain and incubated anaerobically at 37° C. until turbid (about 16 to about 24 hours). The broth cultures were aseptically streaked onto Congo Red Agar plates and incubated anaerobically at 37° C. for 48 hours. It is believed that EPS produced as a by-product of the growth and/or metabolism of certain strains prevents the uptake of the Congo red stain resulting in a cream/white colony morphology. Stains that produce less EPS take up the Congo red stain easily, resulting in a pink/red colony morphology. Strains that do not produce an EPS stain red and look almost transparent in the red agar background.

Figure 2:
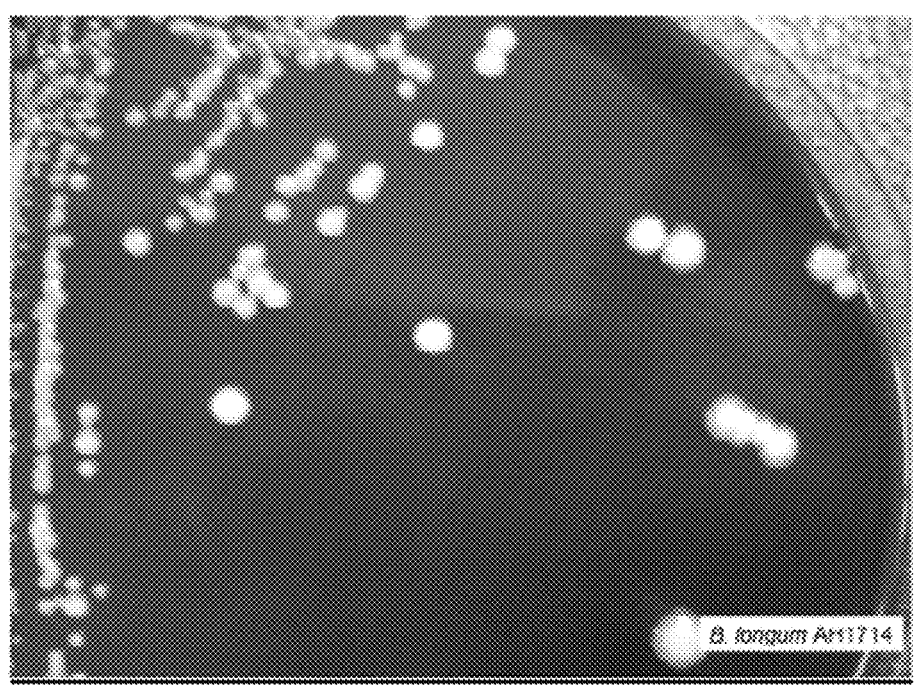
FIG. 2 is a photograph of *B. longum* AH1714 grown on a Congo Red Agar plate.

Referring to FIG. 2 the colony morphology for *B. longum* AH1714 is convex, mucoid, bright white colonies Example 3—Bifidobacteria 1714 Induces a Significantly Elevated IL-10:IL-12 Ratio Peripheral blood mononuclear cells (PBMCs) were isolated from healthy human peripheral blood using BD Vacutainer CPT tubes (BD catalog 362761), as per the manufacturer's instructions. PBMCs were washed and resuspended in Dulbecco's Modified Eagle Medium—Glutamax™ (Glutamax (Glutamine substitute)+pyruvate+4.5 g/l glucose (Gibco catalog 10569-010) 10% fetal bovine serum (Sigma catalog F4135), and 1% penicillin/streptomycin (Sigma catalog P0781). PBMCs were incubated ($2\times10^5$ cells per well) in flat-bottomed 96-well plates and 20 μL of a bacterial suspension (at a concentration of $1\times10^7$ CFU/mL) was added. PBMCs were co-incubated with bacteria for 48 hours at 37° C./5% $CO_2$ in an incubator. After the 2 day incubation period, the plates were centrifuged at 300×g, and the supernatants were removed and stored frozen at −80° C. until analysis. Interleukin-10 (IL-10) and Interleukin-12p70 (IL-12p70) levels in the culture supernatants were quantified using a 96-well assay kit from Meso Scale Discovery (Gaithersburg, Md.; catalog K15008B-1)

Figure 3:
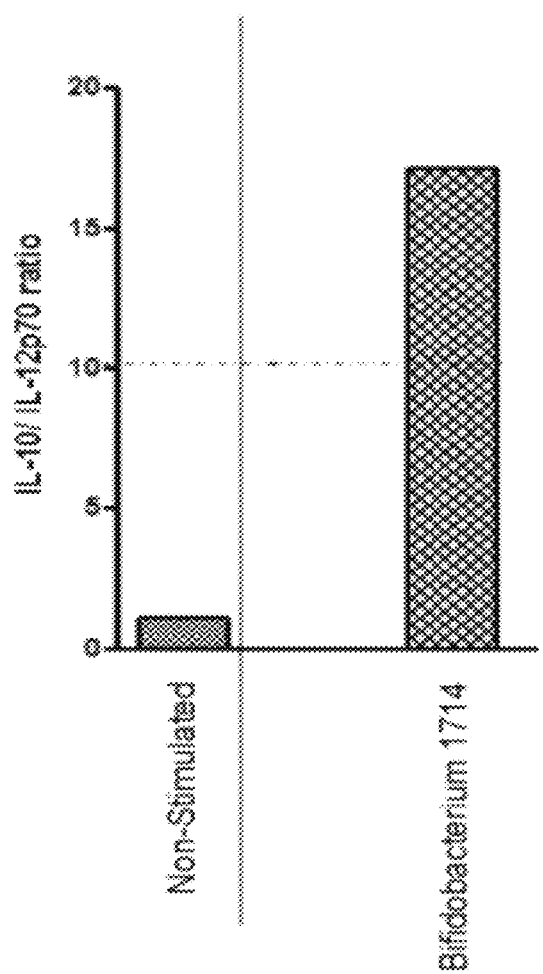
FIG. 3 is a bar chart illustrating the IL-10:IL-12p70 ratio for PBMCs stimulated with *Bifidobacterium* longum strain 1714 (*Bifidobacterium* 1714)

Bacteria were prepared for co-culture experiments in two formats. (a) Freshly grown bacteria were grown in Difco MRS media and harvested just after entering into stationary phase. All cells were grown under anaerobic conditions at 37° C. (b) Bacteria were grown under anaerobic conditions at 37° C. in Difco MRS media and harvested just after entering into stationary phase. Freeze dried powders were generated for each of these bacteria and stored at −80° C. in pre-aliquoted 100 mg vials. Immediately prior to their use, one aliquot of each strain was removed from the freezer and allowed to reach room temperature. Each strain was washed 3 times in 10 ml ringers followed by centrifugation. A fresh vial was used on each occasion. Growth curves (OD vs number of live cells) were constructed for each growth condition, and washed cells were normalized by cell number before addition to the PBMCs. A no-bacteria control was also included in all experiments. All assays were done in triplicate. The results are presented in FIG. 3.

The control of inflammatory diseases is exerted at a number of levels. The controlling factors include hormones, prostaglandins, reactive oxygen and nitrogen intermediates, leukotrienes and cytokines. Cytokines are low molecular weight biologically active proteins that are involved in the generation and control of immunological and inflammatory responses. A number of cell types produce these cytokines, with neutrophils, monocytes and lymphocytes being the major sources during inflammatory reactions due to their large numbers at the injured site.

Multiple mechanisms exist by which cytokines generated at inflammatory sites influence the inflammatory response. Chemotaxis stimulates homing of inflammatory cells to the injured site, whilst certain cytokines promote infiltration of cells into tissue. Cytokines released within the injured tissue result in activation of the inflammatory infiltrate. Most cytokines are pleiotropic and express multiple biologically overlapping activities. As uncontrolled inflammatory responses can result in diseases such as IBD, it is reasonable to expect that cytokine production has gone astray in individuals affected with these diseases.

Interleukin-10 (IL-10) is an anti-inflammatory cytokine which is produced by many cell types including monocytes, macrophages, dendritic cells, mast cells and lymphocytes (in particular T regulatory cells). IL-10 down-regulates the expression of pro-inflammatory Th1 cytokines, MHC class II antigens, and co-stimulatory molecules on antigen presenting cells. It also enhances B cell survival, proliferation, and antibody production. This cytokine can block NF-κB activity, and is involved in the regulation of the JAK-STAT signaling pathway. Murine knock-out studies have demonstrated the essential role for IL-10 in immunoregulation as IL-10KO mice develop severe colitis. In addition, bacteria which are potent inducers of IL-10 have been shown to promote T regulatory cell differentiation in vivo thus contributing to immunological homeostasis (7; 8). Interleukin-12 (IL-12) is a pro-inflammatory cytokine associated with polarisation of Th1 effector T cell responses and stimulates the production of other pro-inflammatory Th1 cytokines, such as interferon-gamma (IFN-γ) and tumor necrosis factor-alpha (TNF-α), from T and natural killer (NK) cells. High levels of IL-12 expression is associated with autoimmunity. Administration of IL-12 to people suffering from autoimmune diseases was shown to worsen disease symptoms. In contrast, IL-12 knock-out mice or treatment of mice with IL-12 neutralising antibodies ameliorated the disease.

Cytokine cascades and networks control the inflammatory response, rather than the action of a particular cytokine on a particular cell type. The relative levels of expression, or balance, of two cytokines (such as IL-10 and IL-12) is more informative than the expression of a single cytokine. In these studies, we stimulated human PBMCs with a range of different bacterial strains. All strains induced IL-10 and all strains induced IL-12. However, examination of the ratio between IL-10 and IL-12 induction revealed that some bacterial strains induced a higher ratio (i.e. more IL-10 with less IL-12) compared to other strains. This is a meaningful observation as it is the balance between each of these opposing signals that ultimately determines the immunological outcome. It is anticipated that a high IL-10:IL-12 ratio would promote an anti-inflammatory response associated with appropriate immunoregulatory activity while a low IL-10:IL-12 ratio would contribute to Th1 polarisation of the immune response. Thus, the PBMC IL-10:IL-12 ratio is a important selection criterion for identification of bacterial strains with immunoregulatory properties.

Example 4—Long Term Feeding of Mice with Bif. AH1714 is Associated with Increased Anti-Inflammatory Cytokine IL-10 and with Decreased Pro-Inflammatory and Th1 Cytokines TNF-α☐ IFN-γ and IL-12 in Healthy Animals and in a Model of Sepsis/Inflammation Materials & Methods:

Female Balb/c mice @ 6-8 weeks of age are sourced from Harlan UK and housed in individually ventilated cages and provided ad libitum access to sterile standard mouse chow and water.

Mice of similar weight are randomised into 2 groups and administered PBS (carrier control n=9), *Bifidobacterium longum* strain AH1714 (n=17) via oral gavage on a daily basis for 115 days. Following the period of administration blood is sampled from 10 AH1714 mice and 6 carrier controls were challenged with 1 mg/kg LPS (Sigma, L4391) via intra peritoneal injection.

Following the period of administration blood is sampled from 6 AH1714 mice and 4 carrier controls, serum is extracted and preserved for cytokine measurements. Spleens are also removed and single cell suspensions cultured in vitro. Cytokines are measured in cell supernatants following 48 hours culturing.

A further 10 AH1714 mice and 6 control mice are administered a single dose of LPS@1 mg/kg via intraperitoneal injection. After 2 hours blood is sampled and the mice were culled. Serum and splenocyte cells were treated and analysed as previously described.

Splenocyte Cytokine Assay

Splenocytes are isolated from spleens and incubated for 48 hours at 37° C. (in the presence of penicillin and streptomycin) with control media, LPS, or antiCD3/CD28. Cytokines in the culture supernatants are assayed using a 96-well assay kit from Meso Scale Discovery (Gaithersburg, Md.; catalog K15008B-1). Interleukin 1 beta (Il-1b), Interleukin 6 (Il-6), Interleukin 8 (Il-8) Interleukin 10 (Il-10), Interleukin 12p70 (Il12p70), Interferon-gamma (IFN-γ) and Tumor Necrosis Factor alpha (TNF☐) are quantitated and reported as picograms per milliliter (pg/mL).

Serum Cytokine Assay

Serum is analysed using the Meso Scale Discovery mouse IL-10 and TNF-α Ultrasensitive kit.

Results

Figure 4:
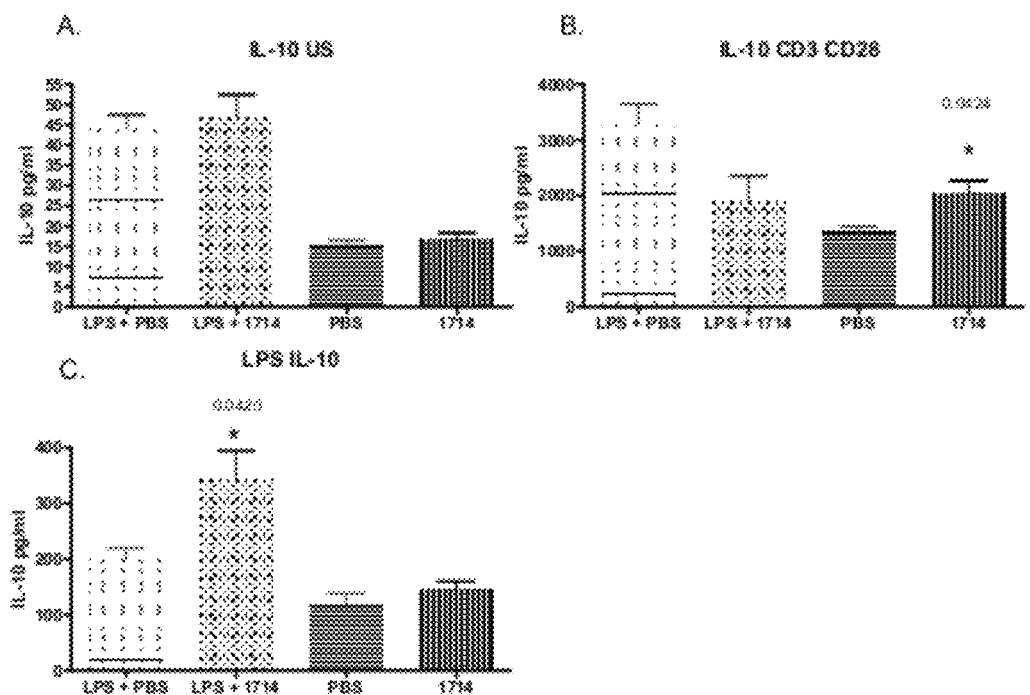
FIG. 4 is a bar chart showing the induction profile of IL-10 in splenocytes isolated from both 1714 and PBS fed mice with and without in vivo LPS challenge 1 mg/kg. In vitro cells are either unstimulated (A), stimulated with LPS (B) or stimulated with antiCD3/CD28 (C). Data is shown as Average & SEM.

Long term feeding of mice (115 days) with Bif. AH1714 is associated with an increase in the anti-inflammatory cytokine IL-10 from stimulated ex vivo PBMCs, compared to placebo group (fed PBS) for healthy mice (See FIG. 4 (B)) or in a Sepsis/Inflammation model (mice challenged with LPS; See FIG. 4 (C)).

Figure 5:
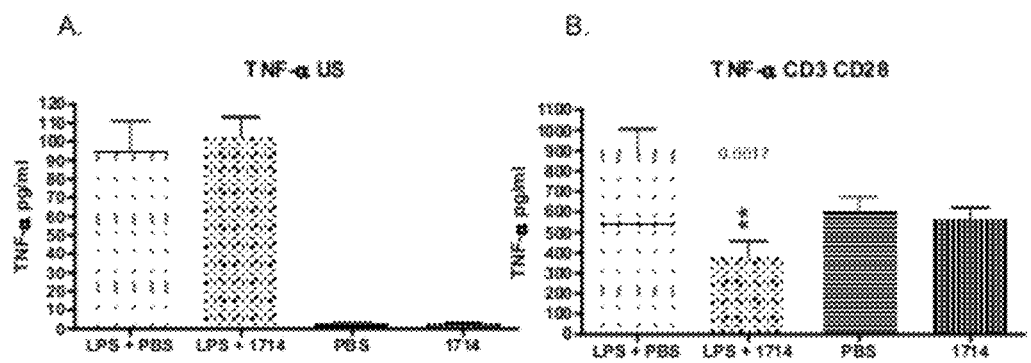
FIG. 5 is a bar chart showing the induction profile of TNF-α in splenocytes isolated from both 1714 and PBS fed mice with and without in vivo LPS challenge 1 mg/kg. In vitro cells are either unstimulated (A) or stimulated with antiCD3/CD28 (B). Data is shown as Average & SEM.
Figure 6:
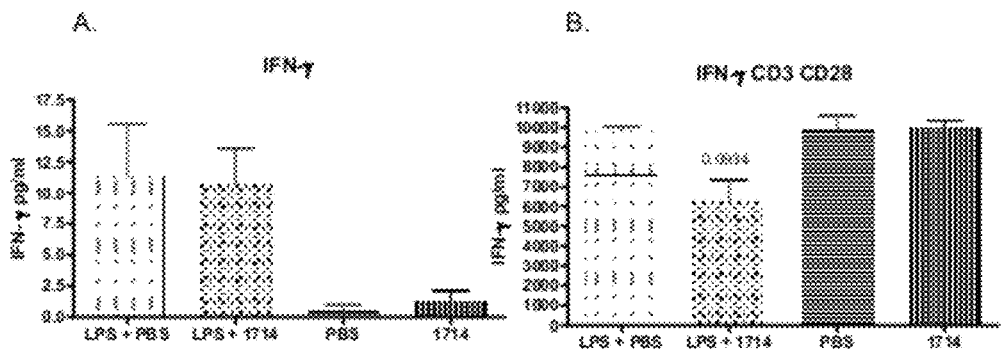
FIG. 6 is a bar chart showing the induction profile of IFN-γ in splenocytes isolated from both 1714 and PBS fed mice with and without in vivo LPS challenge 1 mg/kg. In vitro cells are either unstimulated (A) or stimulated with antiCD3/CD28 (B). Data is shown as Average & SEM.
Figure 7:
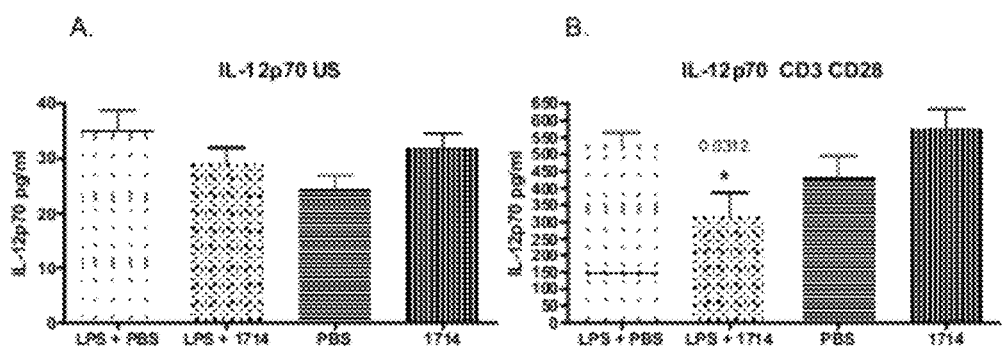
FIG. 7 is a bar chart showing the induction profile of IL-12p70 in splenocytes isolated from both 1714 and PBS fed mice with and without in vivo LPS challenge 1 mg/kg.

Long term feeding of mice (115 days) with Bif. AH1714 is associated with a decrease in the pro-inflammatory and Th1 cytokines TNF-α☐ IFN-γ and IL-12 (p70 sub unit) from stimulated ex vivo PBMCs, compared to placebo group (fed PBS) in a Sepsis/Inflammation model (mice challenged with LPS; See FIG. 5 (B), FIG. 6 (B) and FIG. 7 (B)).

Long term feeding mice (115 days) with Bif. AH1714 is associated with an increase in the serum levels of anti-inflammatory cytokine IL-10 and a decrease in the pro-inflammatory and Th1 cytokine TNF-α, compared to placebo group (fed PBS) in a Sepsis/Inflammation model (mice challenged with LPS; See FIGS. 8 (A & B)).

Taken together, these results demonstrate that *Bifidobacterium longum* strain 1714 has in-vivo systemic immunomodulatory and anti-inflammatory activity and protects against LPS or TLR-4 mediated inflammatory responses.

Example 5—Bif 1714 has Immunomodulatory Activity when Co-Incubated with Human Immune System Cells In Vitro, Different to that of Bif. AH35624

Materials & Methods

*Bifidobacterium longum infantis* strain UCC35624 (B624), two independent culture batches (1 & 2) and *Bifidobacterium longum* strain 1714 is assayed using a PBMC cytokine induction assay. Bacteria are prepared for co-culture experiments in the following formats. Bacteria are grown under anaerobic conditions at 37° C. in Difco MRS Media and harvested just after entering into stationary phase. Freeze dried powders are generated for each of these bacteria and stored at −80° C. in pre-aliquoted 100 mg vials. Immediately prior to their use, one aliquot of each strain is removed from the freezer and allowed to reach room temperature. Each strain is washed 3 times in 10 ml ringers followed by centrifugation. A fresh vial is used on each occasion.

Direct microscopic counts are performed using a Petroff-Hausser counting chamber as per the manufacturer's instructions and washed cells normalized by cell number before addition to the PBMC assay. Bacteria (20 μl in phosphate buffered saline (PBS)) are added to each well of PBMCs to give the total number of bacteria as indicated for each experiment.

PBMC (Peripheral Blood Mononuclear Cell) Cytokine Induction Assay

Peripheral blood mononuclear cells (PBMCs) are isolated from healthy human peripheral blood using BD Vacutainer CPT tubes (BD catalog 362761), as per the manufacturer's instructions. PBMCs are washed and resuspended in Dulbecco's Modified Eagle Medium—Glutamax™ (Glutamax (Glutamine substitute)+pyruvate+4.5 g/l glucose (Gibco catalog 10569-010) 10% fetal bovine serum (Sigma catalog F4135), and 1% penicillin/streptomycin (Sigma catalog P0781). PBMCs are incubated ($2\times10^5$ cells per well) in flat-bottomed 96-well plates and 20 μL of a bacterial suspension. A no-bacteria control also is run. All assays are done in triplicate. After a 2-day incubation at 37° C., the plates were spun at 300×g, and the supernatants were removed and stored frozen at −80° C. until analysis. PBMCs are co-incubated with bacteria for 48 hours at 37° C./5% $CO^2$ in an incubator. After the 2 day incubation period, the plates are centrifuged at 300×g, and the supernatants removed and stored frozen at −80° C. until analysis. Cytokines in the culture supernatants are assayed using a 96-well assay kit from Meso Scale Discovery (Gaithersburg, Md.; catalog K15008B-1). Human Interleukin 1 beta (Il-1b), Human Interleukin 6 (Il-6), Human Interleukin 8 (Il-8) Human Interleukin 10 (Il-10), Human Interleukin 12p70 (Il12p70), Human Interferon-gamma (IFN-γ) and Human Tumor Necrosis Factor alpha (TNFα) are quantitated and reported as picograms per milliliter (pg/mL). Each sample is assayed in duplicate.

Results

*Bifidobacterium longum infantis* strain UCC35624 (B624), two independent culture batches (1 & 2) and *Bifi-* dobacterium longum strain 1714 are assayed for immunomodulation using a PBMC cytokine induction assay with 1.0E+07 bacteria. Supernatants are assayed for a range of cytokines, including IL-1β, -6, -8, -10 and -12, TNF-α□ and IFN-γ.

By comparison with 35624 (both cultures of which gave a similar pattern for all cytokines measured), strain 1714 exhibited a very similar pattern for many of the cytokines measured. Surprisingly however, 1714 gave quite a different pattern for IL-12, IFNγ and IL-6.

IL-6:
Incubation with 1714 induces a significantly lower level of IL-6 compared to 35624 at $1.0 \times 10^7$ bacteria per well (See Table 5)

TABLE 5

| Strain (1 × 10E7 bacteria) | IL-6 (~pg/ml) |
|---|---|
| 35624 | 28,000 |
| 1714 | 16,000 |

IL-12:
Incubation with 1714 induces a significantly lower level of IL-12 compared to 35624 at $1.0 \times 10^7$ bacteria per well (See Table 6)

INF-γ
Incubation with 1714 induces a significantly lower level of INF-γ compared to 35624 at $1.0 \times 10^7$ bacteria per well (See Table 6)

TABLE 6

| Strain (1 × 10E7 bacteria) | IL-12 (~pg/ml) | IL-12 (~pg/ml) | IFN-α (~pg/ml) | IFN-γ (~pg/ml) |
|---|---|---|---|---|
| 35624 | 500 | 180 | 5000 | 1500 |
| 1714 (1) | 220 | 115 | 2400 | 750 |
| 1714 (2) | 240 | 80 | 2600 | 400 |

Foligne et al[19], have demonstrated that lactic acid bacteria strains displaying an in vitro capacity to induce higher levels of the anti-inflammatory cytokine IL-10 and lower levels of the inflammatory cytokine IL-12 offered the best protection in the in vivo colitis model whereas in contrast, strains leading to a low IL-10/IL-12 cytokine ratio could not significantly alleviate colitis symptoms. The in vivo protection observed was strain specific. The cytokine profile obtained for Bif. AH1714 would suggest that this strain has the potential for improved efficacy in the in vivo ulcerative colitis model.

IL-6 is a cytokine strongly implicated in the pathology of IBS. L-6 is relevant to many disease processes such as diabetes, atherosclerosis, depression, Alzheimer's Disease, systemic lupus erythematosus and rheumatoid arthritis. Hence there is an interest in developing anti-IL-6 agents as therapy against many of these diseases.

Example 6—Bif. AH1714 Reduces LPS-Induced NFκB Activity in an In-Vivo Murine Sepsis/Inflammation Model Materials & Methods
NFkBlux transgenic mice on a C57BL/6J-CBA/J background are obtained from Charles River Laboratories (Wilmington, USA) and bred in-house. Mice are housed under barrier maintained conditions.

Female animals are administered Bif. AH1714, as a freeze-dried powder reconstituted in water at approximately $1 \times 10^9$ colony forming units/day/animal, or a placebo control. Mice consume the commensal micro-organism in their drinking water ad libitum for 20 days prior to LPS challenge.

NFkB activity is measured following the administration of the substrate luciferin and imaged using the Xenogen IVIS 100. Baseline NFkB activity is measured prior to challenge with a single 0.5 mg/kg dose of LPS. After 3 hours all animals are then reimaged. Whole body NFkB activity is assessed by subtracting baseline readings.

All animals are then culled and spleens, livers, small intestine and colon removed and placed in a culture dish for individual imaging.

Results
Bif. AH1714 reduces systemic LPS-induced NFkB activity in an in-vivo murine Sepsis/Inflammation model as demonstrated by a decreased NFkB activity in spleens isolated 3 hours post challenge (See FIG. 9) and from whole animal imaging 1.5 hours post challenge (See FIG. 10) from 1714-fed animals compared to Placebo-fed animals. These results demonstrate that feeding with Bif. 1714 is associated with a decreased level of systemic inflammation associated with the transcription factor NFkB.

Example 7—1714 Exhibits Positive Benefits in Animal Models of Depression and Anxiety Depression and anxiety are the most common psychiatric disorders with a high prevalence rate in the community. Anxiety disorders are usually subdivided into panic disorder, generalised anxiety disorder, post-traumatic disorder and obsessive compulsive disorder.

Modern antidepressants such as the selective serotonin reuptake inhibitors (e.g. fluoxetine) and selective noradrenergic and serotinergic reuptake inhibitors (e.g. venlafaxine) are widely used to treat these disorders. However, the treatments are not always effective and are not acceptable to patients. There is a need to develop alternative strategies. The possibility that probiotics might be effective in such conditions is suggested by previous data indicating that the probiotic Bifidobacterium Infantis reduces the stress hormone corticosterone in rodents (9).

We here examine the behavioural effects of Bifidobacterium AH1714 in models of stress in mice and compared with a widely used SSRI, namely, escitalopram, which is used to treat both anxiety and depression. Animals are treated with either escitalopram or AH1714 for three weeks.

Material & Methods
Tail Suspension Test
A well characterized test for assessing depression-like and antidepressant like activity. Mice are individually suspended by the tail to a horizontal ring-stand bar (distance from floor=30 cm) using adhesive tape (distance from tip of tail=2 cm). Typically, mice demonstrate several escape-oriented behaviours interspersed with temporally increasing bouts of immobility. A 6-minute test session is employed which is videotaped. Videotapes are subsequently scored by a highly trained observer who is unaware of the treatment. The parameter recorded is the number of seconds spent immobile.

Fear Conditioning Test
Widely used to assess the cognitive components of anxiety disorders. We use a three day protocol which allows for contextual and cue-associated fear learning to be observed. Following 3 minutes of exploring their environmental context mice receiving 6 pairings of 20 seconds of a specific cue (Tone of 10 KHz, 70 dB combined with apparatus light on) coupled at the end with 2 seconds of a mild electrical footshock (0.4 mA), this is followed by 1 min exposure to the context only. The procedure is repeated for two subsequent days, however, no shock is given and freezing behaviour to the context or cue is observed throughout. The first day allows for assessment of the ability of the intervention to alter the strength of context and cue-induced fear conditioning, whereas the third day allows for extinction of fear learning to be observed. Extinction is the formation of new memories and drugs that facilitate extinction may play a role in the treatment of post-traumatic stress disorder.

The Marble-Burping Test

Proposed as model of obsessive compulsive disorder. Animals who are more anxious must engage in active behaviours (defensive marble burying) to avoid anxiogenic stimuli in the light-dark box and elevated mazes. Mice are placed individually in small cages, in which 20 marbles had been equally distributed on top of a 5 cm-deep bed of sawdust, and a wire lid placed on top of the cage. Mice are left undisturbed for 30 min, after which the number of buried marbles (i.e., those more than less than three-quarters covered by sawdust) are counted.

Results

In the tail suspension test AH1714 gives a positive result suggesting possible antidepressant activity. Referring to FIG. 11, AH1714 induced lower immobility time than the vehicle (Veh) which suggests lower depression-like behavious in 1714-fed animals. This is similar to the impact of conventional antidepressants such as Lexapro®.

In terms of cognition, in the fear conditioning test, test animals treated with AH1714 showed a positive learning effect. Referring to FIG. 12, in context (mainly hippocampus and amygdale-dependent memories) fear conditioning tests, 1714 induced higher freezing to the context (Cxt) than the vehicle (Veh) on day 1 and day 2, with the same freezing percentage as the vehicle on day 3, this suggests that 1714 promotes contextual fear learning and memory without impairing extinction, suggesting a positive role in contextual memory of fearful events. Referring to FIG. 13, in cue (amygdale-dependent) fear conditioning tests, 1714 induced higher freezing to the fearful cue (stimulus) than the vehicle (Veh) on day 1, with the same freezing percentage as the vehicle on days 2 and 3. This suggests that 1714 promoted amygdale-dependent (cue) fear learning and memory without impairing memory and extinction, suggesting a positive role in the memory of a fearful stimulus independently of the context.

Evidence of a possible effect in obsessive compulsive disorder emerges from studies with the marble burying test. Animals treated with AH1714 buried less marbles in the marble burying task which is indicative of lower anxiety in 1714-fed animals and suggests a possible effect in obsessive compulsive disorder (FIG. 14). As in the case of escitalopram, AH1714 induced a lower body temperature increase induced by the stress of being handled (decreased stress induced hypothermia) this suggests lower anxiety in 1714-fed animals (FIG. 24). There were no differences between the results with either intervention.

Conclusion

AH1714 in animal models of depression and anxiety behaves in a similar way to a conventional antidepressant. The impact observed is similar to that reported in the literature for antidepressants such as SSRIs.

Overall, the data indicate that AH1714 may be of benefit in the treatment of the psychiatric syndromes of depression and anxiety.

Example 8—1714 Exhibits Positive Benefits on Inflammatory Markers in Diet-Induced Obesity In recent years, it has been well established that obesity is associated with a low-grade inflammation that contributes to the development of the pathologies associated with obesity which include type 2 diabetes mellitus (T2D), cardiovascular disease (CVD), hypertension, hypercholesterolemia, hypertriglyceridemia, and non-alcoholic fatty liver disease (NAFLD). Visceral fat produces a number of inflammatory cytokines and chemokines (such as leptin, tumor necrosis factor-α (TNF-α), macrophage chemo-attractant protein-1 and interleukin-6, among others), whose production can be pathologically dysregulated in the obese state (reviewed by Shoelson et al., 2007). Indeed, while macrophages are thought to contribute in an important manner to insulin resistance, other studies have suggested that harnessing the anti-inflammatory properties of cells with a potentially regulatory phenotype may have therapeutic potential. A recent study suggests that $T_{reg}$ cells reduce the inflammatory state of adipose tissue and, thus, insulin resistance in mice (Feurer et al., 2009). In addition, a seminal body of work has implicated abnormalities of the gut microbiota as a driving force of obesity-related metabolic dysregulation, suggesting that interventions which target gut health will have beneficial health effects in obesity related metabolic derangements. It has been suggested that the gut microbiota may be involved in the development of obesity in the regulation of energy homeostasis, in insulin resistance, non-alcoholic fatty liver disease and in energy, lipid and amino acid metabolism (reviewed by Ley et al., 2009)

The Diet-Induced Obesity (DIO) mouse model was chosen as the most appropriate mouse model for assessing the impact of selected probiotic candidates on obesity and metabolic health and to look at the relationship between obesity and inflammatory markers. The DIO mouse model refers to healthy mice fed a high-fat diet to induce obesity over time.

Experimental Design

Seven-week old male C57BL/J6 mice were fed a low-fat diet (10% calories from fat; Research Diets, New Jersey; #D12450B), a high-fat diet (DIO; 45% calories from fat; Research Diets, New Jersey; #D12451) or a high-fat diet with AH1714 ($1\times10^9$ cfu/day) in drinking water for 14 weeks. All mice were housed in groups of 5 and fresh probiotic aliquots were administered daily. Body weight and food intake were assessed weekly. At the end of 14 weeks the mice were sacrificed and internal organs were removed, weighed and stored at −80° C. The spleens removed and splenocyte cytokine assays were carried out as in example 4.

Results

As expected, DIO mice gained significantly more fat mass ($p<0.001$) compared to lean controls over the 14-week feeding period. In agreement with previous studies, DIO mice consumed significantly more calories than lean controls, as measured by the cumulative caloric intake over the 14 week period of the study ($p<0.001$). In LPS stimulated splenocytes (innate immunity stimulus) from DIO mice, AH1714 had the effect of lowering the TNFα and IL-12 cytokine response to LPS (FIG. 16). In CD3/CD28 stimulated spenocytes (adaptive immunity stimulus), treatment with AH1714 had the effect of lowering the IL6 cytokine response. These results indicate a systemic anti-inflammatory effect in the DIO mouse model consistent with the PBMC data and in vivo mouse model data illustrated in other examples.

Immunomodulation

The human immune system plays a significant role in the aetiology and pathology of a vast range of human diseases. Hyper and hypo-immune responsiveness results in, or is a component of, the majority of disease states. One family of biological entities, termed cytokines, are particularly important to the control of immune processes. Pertubances of these delicate cytokine networks are being increasingly associated with many diseases. These diseases include but are not limited to inflammatory disorders, immunodeficiency, inflammatory bowel disease, irritable bowel syndrome, cancer (particularly those of the gastrointestinal and immune systems), diarrhoeal disease, antibiotic associated diarrhoea, paediatric diarrhoea, appendicitis, autoimmune disorders, multiple sclerosis, Alzheimer's disease, rheumatoid arthritis, coeliac disease, diabetes mellitus, organ transplantation, bacterial infections, viral infections, fungal infections, periodontal disease, urogenital disease, sexually transmitted disease, HIV infection, HIV replication, HIV associated diarrhoea, surgical associated trauma, surgical-induced metastatic disease, sepsis, weight loss, anorexia, fever control, cachexia, wound healing, ulcers, gut barrier function, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, epidermal disorders, psoriasis and acne vulgaris.

The effects on cytokine production are specific for each of the probiotic strains examined. Thus specific probiotic strains may be selected for normalising an exclusive cytokine imbalance particular for a specific disease type. Customisation of disease specific therapies can be accomplished using either a single strain of AH1714 or mutants or variants thereof or a selection of these strains.

Immune Education

The enteric flora is important to the development and proper function of the intestinal immune system. In the absence of an enteric flora, the intestinal immune system is underdeveloped, as demonstrated in germ free animal models, and certain functional parameters are diminished, such as macrophage phagocytic ability and immunoglobulin production (10). The importance of the gut flora in stimulating non-damaging immune responses is becoming more evident. The increase in incidence and severity of allergies in the western world has been linked with an increase in hygiene and sanitation, concomitant with a decrease in the number and range of infectious challenges encountered by the host. This lack of immune stimulation may allow the host to react to non-pathogenic, but antigenic, agents resulting in allergy or autoimmunity. Deliberate consumption of a series of non-pathogenic immunomodulatory bacteria would provide the host with the necessary and appropriate educational stimuli for proper development and control of immune function.

Inflammation

Inflammation is the term used to describe the local accumulation of fluid, plasma proteins and white blood cells at a site that has sustained physical damage, infection or where there is an ongoing immune response. Control of the inflammatory response is exerted on a number of levels (11). The controlling factors include cytokines, hormones (e.g. hydrocortisone), prostaglandins, reactive intermediates and leukotrienes. Cytokines are low molecular weight biologically active proteins that are involved in the generation and control of immunological and inflammatory responses, while also regulating development, tissue repair and haematopoiesis. They provide a means of communication between leukocytes themselves and also with other cell types. Most cytokines are pleiotrophic and express multiple biologically overlapping activities. Cytokine cascades and networks control the inflammatory response rather than the action of a particular cytokine on a particular cell type (12). Waning of the inflammatory response results in lower concentrations of the appropriate activating signals and other inflammatory mediators leading to the cessation of the inflammatory response. TNFα is a pivotal proinflammatory cytokine as it initiates a cascade of cytokines and biological effects resulting in the inflammatory state. Therefore, agents which inhibit TNFα are currently being used for the treatment of inflammatory diseases, e.g. infliximab.

Pro-inflammatory cytokines are thought to play a major role in the pathogenesis of many inflammatory diseases, including inflammatory bowel disease (IBD). Current therapies for treating IBD are aimed at reducing the levels of these pro-inflammatory cytokines, including IL-8 and TNFα. Such therapies may also play a significant role in the treatment of systemic inflammatory diseases such as rheumatoid arthritis.

The strains of the present invention may have potential application in the treatment of a range of inflammatory diseases, particularly if used in combination with other anti-inflammatory therapies, such as non-steroid anti-inflammatory drugs (NSAIDs) or Infliximab.

Cytokines and Cancer

The production of multifunctional cytokines across a wide spectrum of tumour types suggests that significant inflammatory responses are ongoing in patients with cancer. It is currently unclear what protective effect this response has against the growth and development of tumour cells in vivo. However, these inflammatory responses could adversely affect the tumour-bearing host. Complex cytokine interactions are involved in the regulation of cytokine production and cell proliferation within tumour and normal tissues (13, 14). It has long been recognized that weight loss (cachexia) is the single most common cause of death in patients with cancer and initial malnutrition indicates a poor prognosis. For a tumour to grow and spread it must induce the formation of new blood vessels and degrade the extracellular matrix. The inflammatory response may have significant roles to play in the above mechanisms, thus contributing to the decline of the host and progression of the tumour. Due to the anti-inflammatory properties of *Bifidobacterium longum infantis* these bacterial strains they may reduce the rate of malignant cell transformation. Furthermore, intestinal bacteria can produce, from dietary compounds, substances with genotoxic, carcinogenic and tumour-promoting activity and gut bacteria can activate pro-carcinogens to DNA reactive agents (15). In general, species of *Bifidobacterium* have low activities of xenobiotic metabolizing enzymes compared to other populations within the gut such as bacteroides, eubacteria and clostridia. Therefore, increasing the number of *Bifidobacterium* bacteria in the gut could beneficially modify the levels of these enzymes.

Vaccine/Drug Delivery

The majority of pathogenic organisms gain entry via mucosal surfaces. Efficient vaccination of these sites protects against invasion by a particular infectious agent. Oral vaccination strategies have concentrated, to date, on the use of attenuated live pathogenic organisms or purified encapsulated antigens (16). Probiotic bacteria, engineered to produce antigens from an infectious agent, in vivo, may provide an attractive alternative as these bacteria are considered to be safe for human consumption (GRAS status).

Murine studies have demonstrated that consumption of probiotic bacteria expressing foreign antigens can elicit protective immune responses. The gene encoding tetanus toxin fragment C (TTFC) was expressed in *Lactococcus lactis* and mice were immunized via the oral route. This system was able to induce antibody titers significantly high enough to protect the mice from lethal toxin challenge. In addition to antigen presentation, live bacterial vectors can produce bioactive compounds, such as immunostimulatory cytokines, in vivo. *L. lactis* secreting bioactive human IL-2 or IL-6 and TTFC induced 10-15 fold higher serum IgG titres in mice immunized intranasally (17). However, with this particular bacterial strain, the total IgA level was not increased by coexpression with these cytokines. Other bacterial strains, such as *Streptococcus gordonii*, are also being examined for their usefulness as mucosal vaccines. Recombinant *S. gordonii* colonizing the murine oral and vaginal cavities induced both mucosal and systemic antibody responses to antigens expressed by this bacterial (18). Thus oral immunization using probiotic bacteria as vectors would not only protect the host from infection, but may replace the immunological stimuli that the pathogen would normally elicit thus contributing to the immunological education of the host.

Prebiotics

The introduction of probiotic organisms is accomplished by the ingestion of the micro-organism in a suitable carrier. It would be advantageous to provide a medium that would promote the growth of these probiotic strains in the large bowel. The addition of one or more oligosaccharides, polysaccharides, or other prebiotics enhances the growth of lactic acid bacteria in the gastrointestinal tract. Prebiotics refers to any non-viable food component that is specifically fermented in the colon by indigenous bacteria thought to be of positive value, e.g. bifidobacteria, lactobacilli. Types of prebiotics may include those that contain fructose, xylose, soya, galactose, glucose and mannose. The combined administration of a probiotic strain with one or more prebiotic compounds may enhance the growth of the administered probiotic in vivo resulting in a more pronounced health benefit, and is termed synbiotic.

Other Active Ingredients

It will be appreciated that the probiotic strains may be administered prophylactically or as a method of treatment either on its own or with other probiotic and/or prebiotic materials as described above. In addition, the bacteria may be used as part of a prophylactic or treatment regime using other active materials such as those used for treating inflammation or other disorders especially those with an immunological involvement. Such combinations may be administered in a single formulation or as separate formulations administered at the same or different times and using the same or different routes of administration.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

REFERENCES

1. McCracken V. J. and Gaskins H. R. Probiotics and the immune system. In: *Probiotics a critical review*, Tannock, G W (ed), Horizon Scientific Press, UK. 1999, p. 85-113.
2. Savage D. C. Interaction between the host and its microbes. In: *Microbial Ecology of the Gut*, Clark and Bauchop (eds), Academic Press, London. 1977, p. 277-310.
3. Kagnoff M. F. Immunology of the intestinal tract. *Gastroenterol.* 1993; 105 (5): 1275-80.
4. Lamm M. E. Interaction of antigens and antibodies at mucosal surfaces. *Ann. Rev. Microbiol.* 1997; 51: 311-40.
5. Raychaudhuri S., Rock K L. Fully mobilizing host defense: building better vaccines. *Nat biotechnol.,* 1998; 16: 1025-31.
6. Stallmach A., Strober W, MacDonald T T, Lochs H, Zeitz M. Induction and modulation of gastrointestinal inflammation. *Immunol. Today,* 1998; 19 (10): 438-41.
7. Liam O'Mahony, Louise O'Callaghan, Jane McCarthy, David Shilling, Paul Scully, Shomik Sibartie, Eamon Kavanagh, William O. Kirwan, Henry Paul Redmond, John Kevin Collins, and Fergus Shanahan. Differential cytokine response from dendritic cells to commensal and pathogenic bacteria in different lymphoid compartments in humans. *Am J Physiol Gastrointest Liver Physiol* 290: G839-G845, 2006.
8. O'Mahony C, Scully P, O'Mahony D, Murphy S, O'Brien F, et al. Commensal-Induced Regulatory T Cells Mediate Protection against Pathogen-Stimulated NF-kB Activation. *PLoS Pathog* 2008, 4(8): e1000112.
9. Desbonnet L, Garrett L, Clarke G, Bienenstock J, Dinan T G. The probiotic Bifidobacteria infantis: An assessment of potential antidepressant properties in the rat. *J Psychiatr Res.* 2008 December; 43(2):164-74.
10. Crabbe P. A., H. Bazin, H. Eyssen, and J. F. Heremans. The normal microbial flora as a major stimulus for proliferation of plasma cells synthesizing IgA in the gut. The germ free intestinal tract. *Into. Arch. Allergy Appl Immunol,* 1968; 34: 362-75.
11. Henderson B., Poole, S and Wilson M. 1998. In "Bacteria-Cytokine interactions in health and disease. Portland Press, 79-130.
12. Arai K I, Lee F, Miyajima A, Miyatake S, Arai N, Yokota T. Cytokines: coordinators of immune and inflammatory responses. *Annu Rev Biochem* 1990; 59:783-836.
13. McGee D W, Bamberg T, Vitkus S J, McGhee J R. A synergistic relationship between TNF-alpha, IL-1 beta, and TGF-beta 1 on IL-6 secretion by the IEC-6 intestinal epithelial cell line. *Immunology* 1995 September; 86(1): 6-11.
14. Wu S, Meeker W A, Wiener J R, Berchuck A, Bast R C Jr, Boyer C M. Transfection of ovarian cancer cells with tumour necrosis factor alpha (TNF-alpha) antisense mRNA abolishes the proliferative response to interleukin-1 (IL-1) but not TNF-alpha. *Gynecol Oncol* 1994 April; 53(1):59-63.
15. Rowland I. R. Toxicology of the colon: role of the intestinal microflora. In: Gibson G. R. (ed). *Human colonic bacteria: role in nutrition, physiology and pathology*, 1995, pp 155-174. Boca Raton CRC Press.
16. Walker, R. I. New strategies for using mucosal vaccination to achieve more effective immunization. *Vaccine*, 1994; 12: 387-400.
17. Steidler L., K. Robinson, L. Chamberlain, K. M Scholfield, E. Remaut, R. W. F. Le Page and J. M. Wells. Mucosal delivery of murine interleukin-2 (IL-2) and IL-6 by recombinant strains of Lactococcus lactis coexpressing antigen and cytokine. *Infect. Immun.*, 1998; 66:3183-9.
18. Medaglini D., G. Pozzi, T. P. King and V. A. Fischetti. Mucosal and systemic immune responses to a recombinant protein expressed on the surface of the oral commensal bacterium Streptococcus gordonii after oral colonization. *Proc. Natl. Acad. Sci. USA*, 1995; 92:6868-72
McCracken V. J. and Gaskins H. R, 'Probiotics a critical review', Horizon Scientific Press, UK 1999, p. 278.
19. Foligne, B., Nutten, S., Grangette, C., Dennin V., Goudercourt, D., Poiret, S., Dewulf, J., Brassart, D., Mercenier, A., and Pot, B., Correlation between in vitro and in vivo immunomodulatory properties of lactic acid bacteria. *World J. Gastroenterol.* 2007; 13(2): 236-243.
20. Feuerer M, Herrero L, Cipolletta D, Naaz A, Wong J, Nayer A, Lee J, Goldfine A B, Benoist C, Shoelson S, Mathis D. Lean, but not obese, fat is enriched for a unique population of regulatory T cells that affect metabolic parameters. *Nature Medicine* (2009) 15, 930-939.
21. Shoelson S E, Herrero L, Naaz A. Obesity, inflammation, and insulin resistance. *Gastroenterology* (2007) 132, 2169-2180.
22. Ley R E. Obesity and the human microbiome. *Curr Opin Gastroenterol.* (2010) 1, 5-11.

What is claimed is:

1. A formulation for oral administration to a human, the formulation comprising isolated strain *Bifidobacterium longum* AH1714 deposited with NCIMB under accession number NCIMB 41676 and an ingestible carrier, wherein the formulation is immunomodulatory following oral consumption by the human.

2. The formulation of claim 1, wherein the *Bifidobacterium longum* AH1714 is in the form of viable cells.

3. The formulation of claim 1, wherein the *Bifidobacterium longum* AH1714 is in the form of non-viable cells.

4. The formulation of claim 1, wherein the formulation comprises an additional probiotic material.

5. The formulation of claim 1, wherein the formulation further comprises a prebiotic material.

6. The formulation of claim 1, wherein the ingestible carrier is a pharmaceutically acceptable carrier selected from the group consisting of a capsule, a tablet, and a powder.

7. The formulation of claim 1, wherein the ingestible carrier is a food product selected from the group consisting of acidified milk, yoghurt, frozen yoghurt, milk powder, milk concentrate, cheese spreads, dressings, and beverages.

8. The formulation of claim 1, wherein the formulation further comprises a protein comprising glutamine or glutamate, a peptide comprising glutamine or glutamate, a lipid, a carbohydrate, a vitamin, mineral, a trace element, or a combination thereof.

9. The formulation of claim 1, wherein the *Bifidobacterium longum* AH1714 strain is present in an amount of more than $10^6$ cfu per gram of the formulation.

10. The formulation of claim 1, wherein the formulation further comprises an adjuvant.

11. The formulation of claim 1, wherein the formulation comprises an additional bacterial component.

12. The formulation of claim 1, wherein the formulation further comprises a drug entity.

13. The formulation of claim 1, wherein the formulation comprises an additional biological compound.

14. A foodstuff comprising the formulation of claim 1.

* * * * *